United States Patent
Buijns et al.

(10) Patent No.: US 8,428,220 B2
(45) Date of Patent: Apr. 23, 2013

(54) DYNAMICAL VISUALIZATION OF CORONARY VESSELS AND MYOCARDIAL PERFUSION INFORMATION

(75) Inventors: Antonius Johannes Cornelius Buijns, Best (NL); Peter Maria Johannes Rongen, Eindhoven (NL); Vincent Maurice Andre Auvray, Paris (FR); Odile Bonnefous, Rueil-Malmaison (FR); Raoul Florent, Ville Davray (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 263 days.

(21) Appl. No.: 13/057,772

(22) PCT Filed: Aug. 6, 2009

(86) PCT No.: PCT/IB2009/053444
§ 371 (c)(1),
(2), (4) Date: Feb. 7, 2011

(87) PCT Pub. No.: WO2010/018500
PCT Pub. Date: Feb. 18, 2010

(65) Prior Publication Data
US 2011/0135064 A1    Jun. 9, 2011

(30) Foreign Application Priority Data
Aug. 13, 2008  (EP) .................................. 08305475

(51) Int. Cl.
*H05G 1/64*    (2006.01)
(52) U.S. Cl.
USPC .......................................... 378/98.12; 378/98
(58) Field of Classification Search ............... 378/62, 378/98, 98.11, 98.12; 382/128–132; 600/420
See application file for complete search history.

(56) References Cited

U.S. PATENT DOCUMENTS

| 6,628,743 B1 | 9/2003 | Drummond et al. |
| 6,650,928 B1 | 11/2003 | Gailly et al. |

FOREIGN PATENT DOCUMENTS

| DE | 102005017492 | 4/2007 |
| DE | 102006048606 | 4/2008 |
| DE | 102006046733 | 7/2008 |
| EP | 1901232 | 3/2008 |
| EP | 2082688 | 7/2009 |
| FR | 2914176 | 10/2008 |
| FR | 2924255 | 5/2009 |

(Continued)

OTHER PUBLICATIONS

Schindler et al., "3D Assessment of Myocardial perfusion Parameter combined with 3D Reconstructed Coronary Artery Tree from Digital Coronary Angiograms", International Journal of Cardiac Imaging, 16(1): Feb. 1-12, 2000.

(Continued)

*Primary Examiner* — Courtney Thomas

(57) ABSTRACT

A method for dynamically visualizing coronary information and an apparatus adapted to implement such method is described. In a preferred embodiment of the method, first dynamic cardiac data is acquired during a first cardiac stage and second dynamic cardiac data is acquired during a second cardiac stage. Then, the two data sets are visualized continuously the in a superimposed presentation, wherein the first cardiac data and the second cardiac data corresponding to a same phase within the cardiac cycle are visualized simultaneously. In this way for example information about the vessel geometry may be immediately linked with information about the muscle irrigation or perfusion. Furthermore, this useful information may be displayed in a high-contrasted and low-noise presentation.

14 Claims, 2 Drawing Sheets

FOREIGN PATENT DOCUMENTS

| | | |
|---|---|---|
| JP | 01040033 | 2/1989 |
| JP | 2003164452 | 6/2003 |
| WO | WO2004034329 | 4/2004 |
| WO | WO2005020147 | 3/2005 |

OTHER PUBLICATIONS

Nishimura et al., Superimposed Display of Coronary Artery on Gated Myocardial perfusion Scintigraphy, Journal of Nuclear Medicine, 45(9): 1444-1449 Sep. 2004.

DYNAMICAL VISUALIZATION OF CORONARY VESSELS AND MYOCARDIAL PERFUSION INFORMATION

FIELD OF THE INVENTION

The present invention relates to the field of dynamically visualizing coronary vessels and myocardial perfusion information. Particularly, the present invention relates to a method and an apparatus for acquiring and dynamically visualizing coronary information. Furthermore, the present invention also relates to a computer program element adapted for performing such method when executed on a computer and to a computer-readable medium on which such computer program element is stored.

BACKGROUND OF THE INVENTION

During an examination of the heart it is important to supply accurate images to the physician to facilitate the procedure. A well established method for providing images of the lumen of a vessel is angiography, where after the injection of a contrast agent (CA) a series of images is acquired for example with the help of X-rays.

There are several approaches to provide images with high image quality. An example for such an approach is a procedure known as digital subtraction angiography (DSA), where a first mask image is acquired using for example X-rays, and then, e.g. after injection of a contrast agent into the vessels to be observed, a contrast image is acquired. Subtracting the mask image from the contrast image presents the observer the relevant information only, which is the lumen of a vessel, yielding an image that is more worthwhile to the observer.

As the heart of a living being is a moving object, single images provide snap shots of the organ during different phases of a cardiac cycle. Furthermore, observing the propagation of the contrast agent over several cardiac cycles allows to present images of different stages of a blood circulation (CA propagation), like a coronary stage, a perfusion stage and a venous stage.

The useful acquired information may be low-contrasted, for example during the perfusion stage, the images may be noisy, and the regions of interest may be moving fast with the heart cycle. Furthermore, for a physician looking at the images or image sequences acquired during an examination it may be difficult to correlate the information acquired during the different coronary stages of the blood circulation.

There may be a need for an improved method or apparatus for dynamically visualizing high quality images, in particular images comprising coronary information.

SUMMARY OF THE INVENTION

These needs may be met by the subject-matter according to the independent claims. Advantageous embodiments of the present invention are described in the dependent claims.

According to a first aspect of the present invention, a method for dynamically visualizing coronary information is provided, the method comprising: acquiring first dynamic cardiac data during a first cardiac stage; acquiring second dynamic cardiac data during a second cardiac stage; visualizing continuously the first cardiac data and the second cardiac data in a superimposed presentation; wherein the first cardiac data and the second cardiac data corresponding to a same phase within the cardiac cycle are visualized simultaneously.

In other words the first aspect of the present invention may be seen as based on the idea to superimpose information of a sequence of images gathered during one cardiac stage to a sequence of images gathered during another cardiac stage. The superimposition or overlay of the image sequences is done in such a way that images of the two cardiac stages, which show information of the heart in different cardiac cycles, but in corresponding phases are visualised at the same time. For example with the help of the superimposed images of the different cardiac cycles, information about the vessel geometry (arteries as well as veins) may be linked with information about the muscle irrigation or perfusion.

The coronary information is visualized dynamically, which implies that the raw or processed data is visualised for example on a displaying device like a screen as a sequence of images, e.g. in real time. Coronary artery information may be data concerning the arteries of the heart. Coronary information may concern different phases of a cardiac cycle and may belong to different stages of the blood circulation. Other stages of the blood circulation than the coronary stage can be chosen and superimposed to the original sequences. The visualizing may be done in parallel to the acquisition of the data or alternatively after the acquisition.

The acquisition of data may be the detecting and storing of information about the heart and its vessels, alternatively it may be the gathering of said information from a memory and storing device. In the case of a detecting device a computer tomograph (CT) or any X-ray device may be used.

The acquisition may be continuous in time. For example it can be started after the injection of a contrast agent and/or possibly after a triggering signal derived for example from an electro-cardio-gram (ECG). The starting point of the acquisition can be selected for example with the help of the ECG or alternatively using the data already gathered before. The starting point of the acquisition can be selected at any reference point, for example the beginning of the systole. Then the acquisition may be continued on until no more contrast agent is visible and the data comprising information on the first and second cardiac stages may be extracted or selected hereafter. Alternatively the acquisition may be triggered in such a way that only the first cardiac stage and the second cardiac stage which are of interest are detected. The first and the second cardiac stages may be acquired as a sequence (when they are continuous in time) or separately. A full acquisition may last for example for approximately 15 seconds.

The first and second cardiac stages are not necessarily associated, i.e. the first and second stage are not necessarily followed by each other, there may be several further stages in between the first and the second one.

The dynamic cardiac data may be raw or processed data in two spatial dimensions and one time coordinate. I.e. the dynamic cardiac data may yield information on two-dimensional projections of the heart, its surroundings and its vessels. Furthermore, this data comprises time information, so the state of the heart and the blood circulation may be known at different moments in time. Thus, the motion of the heart may be visualized.

Cardiac stage may refer to information concerning the events related to the flow of blood that occur during the contrast agent propagation, for example the coronary stage, the perfusion stage and the venous stage.

Cardiac cycle may refer to a complete cycle of the heart for example involving the stages of atrial systole, ventricular systole and complete cardiac diastole looping periodically. Cardiac cycles may be defined for example based on ECG signals, which are acquired in parallel to the cardiac data, provided the injection time is known. Alternatively cardiac cycles may be defined or extracted from images, which are based on the acquired cardiac data, for example by analysing extracted features.

Cardiac phase may refer to the state of the heart at a given instant of the cardiac cycle. At a phase the heart is in a given position.

The first cardiac data is data acquired during a first cardiac stage. The second cardiac data is data acquired during at least a cardiac cycle, which is comprised in the second cardiac stage. The first and second cardiac data are visualized continuously in a superimposed presentation. Continuously may denote that a time coordinate is included in the presentation. An example for a continuous presentation may be a "movie" or a presentation in real time as described above, such that a sequence of two dimensional images is displayed at a certain time rate.

The superimposed presentation may be a presentation where two image sequences are overlaid. The presentation may be done on a display or screen, like a computer monitor. In the superimposed presentation the two image sequences are shown simultaneously. The first and second cardiac data may be additionally continuously visualized on further displays, i.e. the data sets are visualized separately.

In the superimposed presentation the first cardiac data and the second cardiac data corresponding to the same phase within the cardiac cycle are visualized simultaneously. This may imply that single images of the image sequences, which show the two-dimensional projection of the heart in the same state of the heart motion are displayed at the same time on the same display. The phase may denote the motion state of the heart. A residual motion (due to breathing, for instance) that has occurred between two time instants corresponding to the same phase can be compensated digitally to ensure a good image alignment.

By visualizing different cardiac data in a superimposed presentation for example the geometry or topology of the cardiac vessels may be overlaid to the information about the myocardial perfusion. Thus, it may be easier for example for a user like a physician to perform a diagnosis. When, for example information of the cardiac vessel topology is displayed together with perfusion data corresponding to the same phase of the heart motion, it may be easier to assess visually, whether the coronary arteries are properly providing the myocardium with blood—and where a possible perfusion problem is coming from. Furthermore, the method as described above may facilitate the assessment of data by providing useful high-contrasted, low-noise information.

According to an embodiment of the invention, the first cardiac stage and the second cardiac stage is a respective one of an arterial stage, a perfusion stage and a venous stage of the coronary information.

For example the first cardiac stage is the arterial stage, and the second cardiac stage corresponds to the sequence of the perfusion stage and the venous stage.

A cardiac stage may denote a period of time where a certain amount or volume of blood, for example the volume with the injected contrast agent, passes certain stages of the blood circulation. Examples for cardiac stages are the arterial stage, the perfusion stage and the vein stage. After the injection of a contrast agent into an artery, the contrast agent can be detected for example for approximately 1.5 seconds in the arteries of the body, this corresponds to the arterial stage. The duration of the stages depends on the amount or volume of the injected contrast agent. After the arterial stage, the blood volume with the contrast agent may flow into the capillary vessels and perfuses a muscle or an organ like the heart, this corresponds to the perfusion stage. When the blood volume with the contrast agent can be detected in the veins for example after leaving the organ, the vein stage starts. There may be further definitions of cardiac stages, depending on their clinical relevance.

According to a further embodiment of the invention the method further comprises determining a transition point between the first cardiac stage and the second cardiac stage; wherein the first cardiac data is acquired before the transition point; and the second cardiac data is acquired after the transition point.

The transition point may be a point in time between the cardiac stages. It may indicate the time, when the overlay may be started. For example it may be the point in time, when the arterial stage has ended and the perfusion stage begins.

In practice there may be difficulties because the cardiac stages may be not well separated. For example, the coronary arteries may still be visible due to the injected contrast agent also after the beginning of perfusion. Thus, in practice the transition point may be chosen such, that the overlay and the superimposed presentation of the data from the different cardiac cycles is started after the end of the arterial stage. For better discrimination of the arterial stage from e.g. the perfusion stage cardiac cycles in between arterial and perfusion stage can be skipped.

The transition point may be determined based on image-based criteria, i.e. on acquired data or alternatively it may be determined based on physical parameters and studies of the human body. The transition point may be determined and set for all measurements or alternatively determined for each measurement separately.

According to a further embodiment the step of continuously visualizing both cardiac data in a superimposed presentation begins during the second cardiac stage.

The continuous visualization of both data sets begins during the second cardiac stage, like for example the perfusion stage. For example, the first cardiac data may be acquired during an arterial stage and possibly visualized on a first display. Then, after the beginning of the second cardiac stage the data acquired during the first cardiac stage may be displayed on a further second display together with the second cardiac data. Possibly, the first cardiac data or parts of it are displayed repeatedly for several times, so as to provide an appropriate overlay of the moving heart vessel topology to the perfusion process. The second cardiac data may be also additionally visualized on a separate display.

According to a further embodiment at least one of the first and second cardiac data is acquired based on an external signal.

The external signal may be an ECG signal acquired for example simultaneously to the dynamic cardiac data. Alternatively the external signal may be any signal comprising information on the motion state or phase of the cardiac cycle being currently measured.

The first or second cardiac data is acquired based on the external signal. This may imply that the acquisition of the data may be triggered based on the information supplied by the external signal.

According to a further embodiment dynamic cardiac data is acquired during a plurality of cardiac cycles and the first cardiac data and the second cardiac data are selected from the acquired data.

For example, the acquisition of data may be triggered or started at the same time or some seconds later than the injection of the contrast agent. Then, dynamic cardiac data is acquired during several cardiac cycles, which again may be included in several different cardiac stages. After or preferably during the acquisition for example with the help of the determination of a transition point as described above, a selection may be made as to when the second cardiac stage starts. This selection may also be made with the help of a ECG signal acquired in parallel to the cardiac data.

According to a further embodiment at least one of the first and second cardiac data is selected based on information comprised in the acquired dynamic cardiac data.

As an alternative to the selection of the cardiac data based on an external signal, the cardiac data may also be selected based on the acquired data itself, like for example based on periodic features, which may be extracted form the images, which are based on the acquired cardiac data.

According to a further embodiment the first cardiac data corresponds to a full cardiac cycle with optimal coronary arteries visibility and the selection of the second cardiac data is based on the selected first cardiac data.

For example the first cardiac data might be the last cardiac cycle before the beginning of the perfusion stage, than the second cardiac data might be the rest of the acquired sequence comprising the perfusion stage. An offset might be included to make sure that the contrast agent still present in the coronary arteries disappears.

The selection of a full cardiac cycle with optimal coronary arteries visibility as the first cardiac data may be advantageous. For example, if the topology of the coronary arteries of the heart is to be overlaid to the perfusion data it may be important to have the best possible visibility of the arteries. Furthermore, the acquisition and/or selection of a full cardiac cycle may be important because in a full cycle the full motion of the heart is represented and may be overlaid several times for example as a time loop to the perfusion data of the second cardiac data. It may be advantageous to select the cardiac cycle with the better or best coronary arteries visibility for example in the filled-in state, when the vessels are full of the blood volume with the contrast agent. To approximately select the optimal cycle, the last cycle before the beginning of the perfusion stage may be selected.

The selection of the second cardiac data is based on the selected first cardiac data. In this way it can for example be ensured that the phase in the beginning of the second cardiac data corresponds to the phase in the beginning of the first cardiac data.

According to a further embodiment the method further comprises performing a background subtraction during the first cardiac stage.

According to a further embodiment the method further comprises performing a background subtraction during the second cardiac stage.

The background subtraction may for example be done with the help of a cardiac digital subtraction angiography (DSA). As described above, mask images may be acquired before the injection of a contrast agent, then after injection of a contrast agent into the vessels to be observed, a contrast image may be acquired. Subtracting the mask images from the contrast images may provide good contrasted vessels filled with the contrast agent. The subtraction of background features may result in images where only the injected coronaries and/or the myocardial perfusion are much better visible.

The first cardiac stage may for example be one or several cycles where arteries are visible following the injection of the contrast agent. In this case the first cardiac data is comprised in the arterial stage and the cardiac DSA is performed to produce images where only the injected contrast agent in the arteries is visible.

The second cardiac data may refer to the images where the contrast agent is delivered into the heart muscle. In this case the second cardiac stage may refer to the perfusion stage and the cardiac DSA is performed to produce images where only the muscle irrigation or perfusion process is visible.

The background subtraction may be a great support and important feature of the method, because it helps to significantly improve the visibility of the vessels and processes in the heart, for example by enhancing the relative contrast of the images.

According to a further embodiment the method further comprises computing spatial correspondence between the first cardiac data and the second cardiac data.

A spatial shift may occur between images based on the first cardiac data and images based on the second cardiac data. The spatial shift may occur for example due to anatomical motions like breathing or patient global motion.

Spatial correspondence of the images may imply that when two images are overlaid in a superimposed presentation, characterising features of the images, like vessels, are located at the same place. When images are visualised with spatial correspondence, the characterising features are in the same spot of the display. For example, when two identical images are visualised with spatial correspondence they are congruent with each other.

One possibility to compute spatial correspondence may be an estimation using a block-matching technique, for example on images retrieved from the dynamic cardiac data before a background subtraction step. After a spatial shift is detected, it may be compensated for.

Alternatively or additionally, in the case that an injection catheter tip is present in both acquired cardiac data sets the computation of spatial correspondence may be based on this visual guide.

The computing of spatial correspondence between the first cardiac data and the second cardiac data allows for better accuracy in the positioning of the vessels like the coronary artery during the visualization of the cardiac data sets in a superimposed presentation.

According to another aspect of the invention an apparatus for acquiring and dynamically visualizing coronary information is provided which is adapted to perform the above-described method.

Such apparatus may include an X-ray source for emitting X-rays, an X-ray detector for acquiring for example X-ray data of an organ, a contrast agent injector for introducing a contrast agent into vessels of a patient, a controlling unit for controlling at least one of the X-ray source, the X-ray detector and the contrast agent injector, a computing unit for example for computing subtraction images and at least one displaying device for visualizing continuously the acquired data in a superimposed presentation.

According to another aspect of the invention a computer program element is presented, which is adapted to perform the method for dynamically visualizing coronary information as described above, when executed on a computer.

According to another aspect of the invention a computer readable medium with a computer program element as described above is presented.

It has to be noted that embodiments of the invention are described with reference to different subject-matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject-matter also any combination between features relating to the different subject-matters, in particular between features of the apparatus type claims and features of the method type claims, is considered to be disclosed with this application.

The aspects defined above and further aspects, features and advantages of the present invention can be derived from the examples of embodiments described hereinafter. The invention will be described in more detail hereinafter with reference to examples of embodiments but to which the invention is not limited.

DETAILED DESCRIPTION OF EMBODIMENTS

Figures 1A, 1B, 1C:
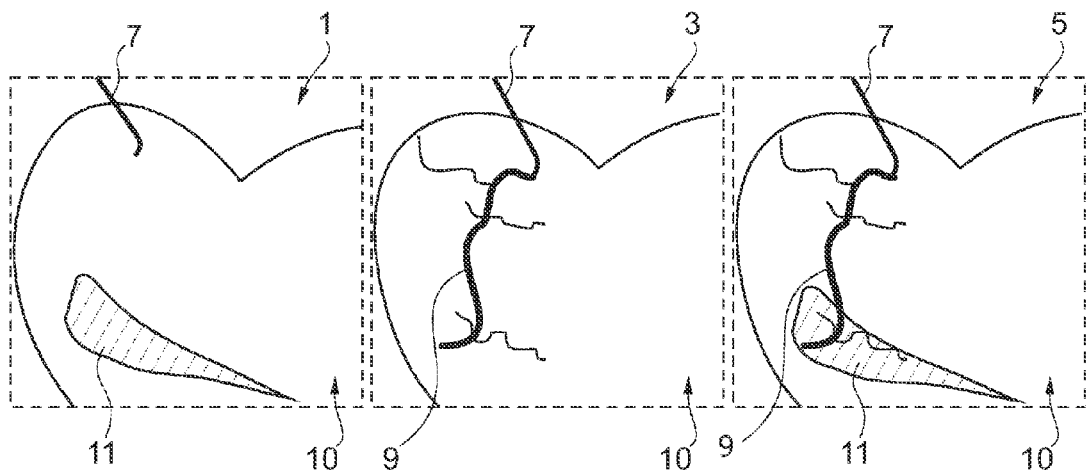
FIG. 1A shows a schematic example of an image acquired with a method according to the present invention during a perfusion stage of the heart.
FIG. 1B shows a schematic example of an image acquired with a method according to the present invention during an arterial inflow of contrast agent into the vessels of the heart.
FIG. 1C shows a schematic example of overlaid images acquired and visualized with a method according to the present invention.

In FIGS. 1A to 1C exemplary snap shots of a continuous presentation, i.e. "movie", of data acquired and visualized with the method according to the invention are presented. In FIG. 1A an image based on data acquired during a perfusion stage of the heart is shown. The image shown in FIG. 1B is based on data acquired during an arterial inflow of contrast agent into the vessels of the heart and the image shown in FIG. 1C shows a snap shot of a continuous overlay of the images shown in FIG. 1A and FIG. 1B.

In the FIG. 1A to 1C a catheter tip 7 is visible. The catheter tip 7 can be used to inject a contrast agent into the vessels 9 of the heart. Furthermore, the catheter tip 7 can be used for medical possibly surgical treatments. The location of the catheter tip 7 is the same in all the images 1A to 1C. Thus, the catheter tip 7 may be used as a helpful orientation to compute spatial correspondence between two images, as for example the image 3 acquired during an arterial stage and image 1 acquired during a perfusion stage. After the acquisition or possibly already during the acquisition the acquired cardiac data is visualised separately, as shown in FIGS. 1A and 1B and in a superimposed or overlay image 5 presentation as shown in FIG. 1C.

If the contrast agent is injected into an artery, as shown in FIG. 1B, a first dynamic cardiac data set corresponding to an image sequence with images similar to the image shown in FIG. 1B can be acquired. Then, during the perfusion of the blood with the contrast agent, a second dynamic cardiac data set corresponding to an image sequence with images similar to the image shown in FIG. 1A can be acquired.

In FIG. 1A the perfusion of the myocardial muscle 11 is visible as the blood volume with the contrast agent leaves the vessels and irrigates the surrounding tissue after the arterial stage shown in FIG. 1B. In FIG. 1C both images from FIGS. 1A and 1B are visualized in a combined superimposed overlay image 5, so as to facilitate the assessment of the condition and processes in the heart for example for a physician. It is in particular of great help for his diagnosis to accurately know the relative position of the coronary arteries with respect to the perfusion basins.

The presentation of the overlay image 5 may be realized in gray scales or in color, wherein the two different images 1 and 3 included in the overlay image 5 may be presented in different colors.

Figure 2:
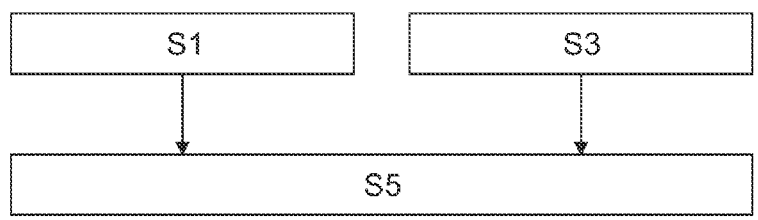
FIG. 2 shows a flow diagram schematically representing a method for dynamically visualizing coronary information according to one exemplary embodiment of the invention.

In FIG. 2 a flow diagram schematically representing a method for dynamically visualizing coronary information according to one exemplary embodiment of the invention is shown. First dynamic cardiac data during a first cardiac cycle is acquired (step S1). At the same time or after the acquisition of the first data, second dynamic cardiac data during a second cardiac cycle is acquired (step S3). As a final step S5 the first cardiac data and the second cardiac data are visualized continuously in a superimposed presentation, with data acquired during the different cardiac cycles corresponding to a same phase visualized simultaneously. A possible result of the visualizing in step S5 is shown in FIG. 1C, wherein FIG. 1C represents only a snap shot of the continuous visualization.

Figure 3:
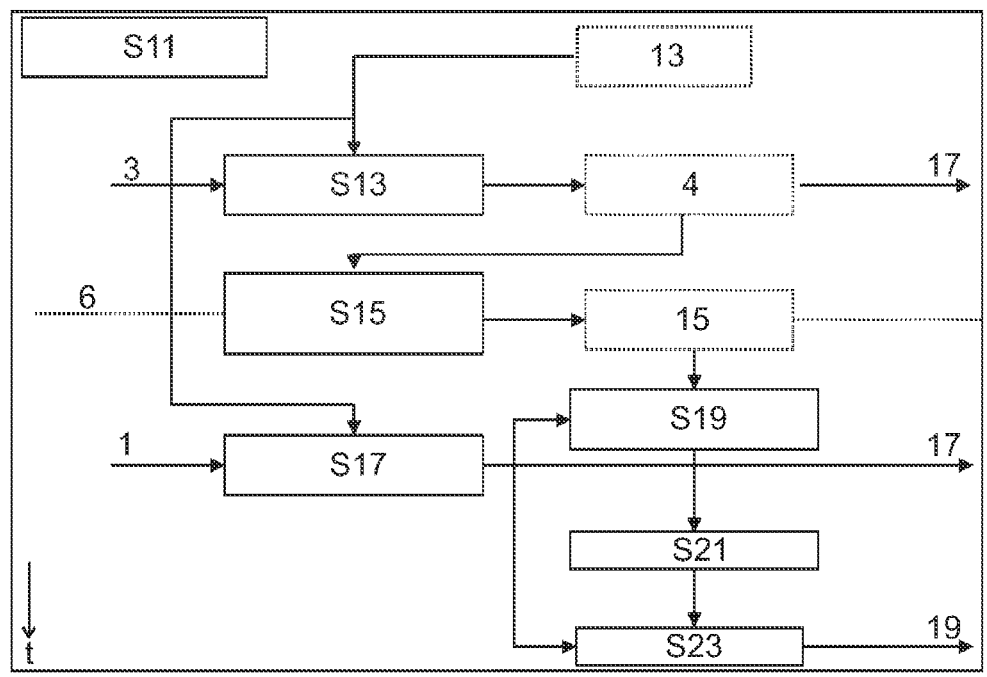
FIG. 3 shows a flow diagram schematically representing a method for dynamically visualizing coronary information according to a further exemplary embodiment of the invention.

In FIG. 3 a flow diagram schematically representing a method for dynamically visualizing coronary information according to a further exemplary embodiment of the invention is shown from which time dependencies between some process steps may be derived. In the example shown in FIG. 3 the method is applied to measurement of perfusion procedures in cardiac angiography. A coronary arterial stage during the arterial stage is extracted from the acquired data and is overlaid to perfusion images also based on the acquired data. This method of visualization considerably helps for example a clinician in his diagnostic task when it comes to assess the perfusion areas in relation with the feeding arteries.

When for example a clinician performs diagnostic cardiac angiographies, he has to assess visually whether the coronary arteries are properly irrigating the cardiac muscle. To do so he has to compare several information: first he has to look for potential artery deformations such as stenosis, which could impair the blood delivery. This is observable during the arterial stage (in the first two seconds) of the contrast agent injection, when the contrast agent progressively fills the considered artery. Additionally, he may also check whether the different regions of the myocardium are correctly irrigated. This can be observed after the arterial stage, in the perfusion stage, when the contrast-injected blood migrates from the coronary arteries to the cardiac muscle. He has then to establish a relationship between those two observations: coronary arteries and myocardial perfusion basins. Some stenoses do not have any impact on the myocardium irrigation (for instance because some collateral vessels have been recruited for substitution blood irrigation) and thus do not necessarily require an intervention. Conversely, unexplained perfusion leakages must be closely investigated.

The exemplary embodiment shown in FIG. 3 may help the clinician in this last task: linking information about the vessel geometry with information about the muscle irrigation, by overlaying during the perfusion stage, the injected coronary veins in the live perfusion image. This might be beneficial both for the determination of the intervention extent, and, in case of intervention, for the outcome control, like the comparison of the perfused areas in relation with the vessels, before and after intervention.

The method according to the exemplary embodiment shown in FIG. 3 delivers as a result an overlay image sequence of the coronary arteries and the perfusion images resulting from the angiographic sequence. A possible snap shot of such an image sequence is shown in FIG. 1C.

In order to achieve this result of overlaying the coronary arteries to the perfusion images the method according to an exemplary embodiment of the invention is patterned as follows:

A coronary stage and a perfusion stage are defined (step S11), possibly before or during the acquisition of the dynamic cardiac data sets. The point in time between the two stages is referred to as transition point 6. To conduct the following calculations it may be useful or necessary to know when the coronary stage has ended (point in time $t_c$), and when the perfusion stage began (point in time $t_p$). A difficulty may arise from the fact that they are not well separated: the coronaries are still visible after the beginning of perfusion. $t_c$ denotes the time of disappearance of the injected coronaries, and $t_p$ denoted the beginning of the perfusion ($t_c > t_p$). The final overlay begins after $t_c$. Those two points in time can be set based on physical studies (since they depend on an anatomical process), and set once for all. Alternatively imagine image-based criteria may be used to define those limits.

Then, an optional background subtraction can be done during the coronary or arterial stage (step S13). During the coronary stage, a cardiac DSA is performed to produce images where the injection only is visible. I(t) denotes the original image also known as mask image 13, and to S(t) the corresponding background subtracted one. The t indicates the time dependency of the dynamical acquisition. The background subtracted images 4 acquired during an arterial stage may be displayed on a separate first display 17 in analogy to the image shown in FIG. 1B.

The background subtraction may be followed by an extraction of a cardiac cycle with optimal coronary arteries visibility (step S15).

Only a full cardiac cycle with injected coronary arteries may be useful for the implementation of the following steps of the method according to the invention. The cardiac cycle may be defined based on the ECG, or alternatively it may be extracted from the image for example by analysing some extracted features.

It may be advantageous to select the cardiac cycle with the better or best coronary arteries visibility (filled-in state). Alternatively it is possible to simply pick the last cycle before the beginning of perfusion ($t_c$). It is also possible to select the most injected cycle even after the perfusion has begun, provided the vessels have been extracted from the perfusion. The selected cardiac cycle 15 is denoted as $C_s$.

The coronary arteries may be also extracted from other image acquisitions or from other image modalities. When the coronary arteries are extracted in this way, methods to synchronize the perfusion image with the coronaries are employed as a further step.

An optional background subtraction can be done during the perfusion stage (step S17). This step may be done in parallel, i.e. at the same time as the background subtraction during the coronary stage or later in time. For example a cardiac DSA may be performed during the perfusion stage, resulting in images S(t) where the perfusion only is visible. In FIG. 3 the images without contrast agent are denoted as mask images 13. The background subtracted images 2 acquired during the perfusion stage may be displayed on a first display 17 in analogy to the image shown in FIG. 1A.

A further possible step is the computation of temporal correspondence between coronary and perfusion images (step S19). For this purpose the coronary image $I_{Cs}(t)$ corresponding to the cardiac stage of the considered perfusion image I(t) may be extracted. The heart position being the same at those phases, the coronary arteries will be positioned at the same spatial location. To find the best match for I(t) in $C_s$, it is for example possible to use an ECG signal or periodic features extracted from the image.

Another possible step, which can follow the computation of temporal correspondence is the computation of spatial correspondence between coronary and perfusion images (step S21).

A spatial shift may occur between images $I_{Cs}(t)$ and I(t), due to anatomical motions like breathing and patient global motion. It may be additionally estimated and compensated for. The estimation may be done using a block-matching technique on the non-subtracted images $I_{Cs}(t)$ and I(t) for example. This step allows for better accuracy in the coronary artery positioning.

Alternatively or additionally, the presence of an injection catheter tip in both the arterial and perfusion stages can be used as a guide in the computation of spatial correspondence. A good match between those two stages also means that the injection tip should be correctly brought into correspondence from one stage to the other. This property may be exploited to enforce or re-enforce good spatial matching.

As a final step, the coronary arteries visible in $I_{Cs}(t)$ are overlaid to the "live", i.e. dynamic perfusion image I(t) and preferably displayed (step S23). If for example no perfusion is present in the subtracted image $S_{Cs}(t)$, a coloured version of $S_{Cs}(t)$ may be added to the images S(t). If the beginning of perfusion is visible in $S_{Cs}(t)$, the vessels may be extracted prior to the overlay step S23.

The overlay result is preferably displayed on a second display 19, next to the first display 17 where the "live" image is displayed. In this way, the clinician may easily rely on it, and ignore it if he doubts its relevance. An example for the overlay result is shown in FIG. 1C.

Figure 4:
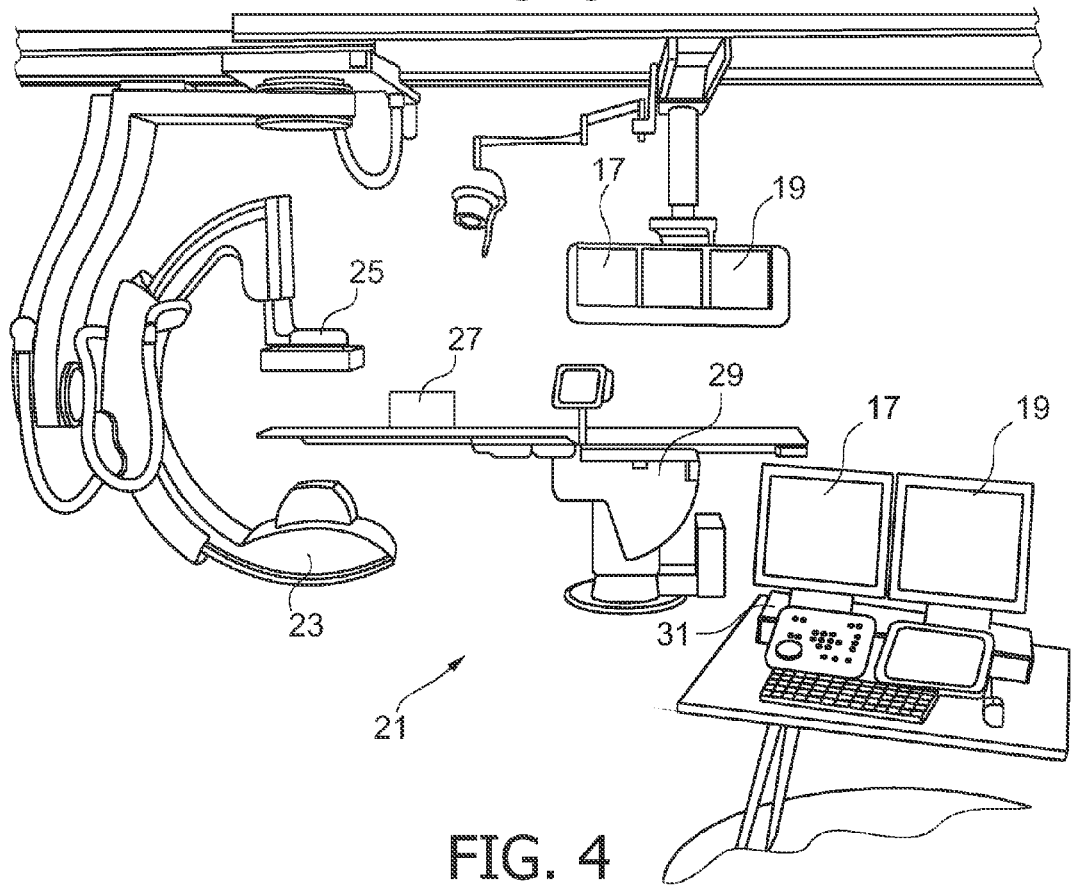
FIG. 4 shows a schematic representation of an apparatus for dynamically visualizing coronary information in a superimposed presentation according to an exemplary embodiment of the present invention.

In FIG. 4 a schematic representation of an apparatus 21 for dynamically visualizing coronary information in a superimposed presentation according to an exemplary embodiment of the present invention is shown.

The apparatus 21 includes an X-ray source 23 for emitting X-rays, an X-ray detector 25 for acquiring for example X-ray data of an organ, a contrast agent injector 27 for introducing a contrast agent into vessels of a patient, a controlling unit 29 for controlling the X-ray source 23, the X-ray detector 25 and the contrast agent injector 27, a computing unit 31 for example for computing subtraction images, a first display 17 for visualizing continuously the images 3 acquired during an arterial stage and also for visualizing continuously the images 1 acquired during a perfusion stage and a second display 19 for visualizing continuously the images 5 of the superimposed presentation. As shown in FIG. 4 the displays 17, 19 may be divided into several further displays or displaying areas. Furthermore, there may be several first displays 17 and several second displays 19.

It should be noted that the terms "comprising", "including" etc. do not exclude other elements or steps and the "a" or "an" does not exclude a plurality. Also elements described in association with different embodiments may be combined. It should also be noted that reference signs in the claims should not be construed as limiting the scope of the claims.

LIST OF REFERENCE SIGNS

1 image during a perfusion stage
2 background subtracted images during a perfusion stage
3 image during an arterial stage
4 background subtracted images during an arterial stage
5 overlay image 6 transition point
7 catheter tip
9 vessels of the heart
11 myocardial muscle
13 mask images
15 images with selected coronary cycle
17 first display
19 second display
21 apparatus
23 X-ray source
25 X-ray detector
27 contrast agent injector
29 controlling unit
31 computing unit
S1 acquiring first dynamic cardiac data during a first cardiac cycle
S3 acquiring second dynamic cardiac data during a second cardiac cycle
S5 visualizing continuously the data sets in a superimposed presentation
S11 definition of a coronary stage and a perfusion stage
S13 background subtraction during the arterial stage
S15 extraction of a cardiac cycle with optimal coronary arteries visibility
S17 background subtraction the perfusion stage
S19 computation of temporal correspondence
S21 computation of spatial correspondence
S23 overlaying and visualizing the images

The invention claimed is:

1. A method for dynamically visualizing coronary information, the method comprising:
    acquiring first dynamic cardiac data during a first cardiac stage during which a contrast agent is detected in a first region;
    acquiring second dynamic cardiac data during a second cardiac stage during which said contrast agent is detected in a second region;
    visualizing continuously the first cardiac data and the second cardiac data in a superimposed presentation which shows both the first and second regions with the contrast agent;
    wherein the first cardiac data and the second cardiac data corresponding to a same phase within a cardiac cycle are visualized simultaneously and wherein a cardiac stage defines a period of time where a certain amount or volume of blood with the contrast agent, passes certain stages of blood circulation.

2. The method according to claim 1,
    wherein the first cardiac stage and the second cardiac stage is a respective one of an arterial stage, a perfusion stage and a vein stage of the coronary information.

3. The method according to claim 2, further comprising determining a transition point between the first cardiac stage and the second cardiac stage;
    wherein the first cardiac data is acquired before the transition point; and
    wherein the second cardiac data is acquired after the transition point.

4. The method according to claim 2,
    wherein the step of continuously visualizing both cardiac data in a superimposed presentation begins during the second cardiac stage.

5. The method according to claim 1,
    wherein at least one of the first and second cardiac data is acquired based on an external signal.

6. The method according to claim 1,
    wherein dynamic cardiac data is acquired during a plurality of cardiac cycles; and
    wherein the first cardiac data and the second cardiac data are selected from the acquired data.

7. The method according to claim 6,
    wherein at least one of the first and second cardiac data is selected based on information comprised in the acquired dynamic cardiac data.

8. The method according to claim 6,
    wherein the first cardiac data corresponds to a full cardiac cycle with optimal coronary arteries visibility; and
    wherein the selection of the second cardiac data is based on the selected first cardiac data.

9. The method according to claim 1, further comprising performing a background subtraction during the first cardiac stage.

10. The method according to claim 1, further comprising performing a background subtraction during the second cardiac stage.

11. The method according to claim 1, further comprising computing spatial correspondence between the first cardiac data and the second cardiac data, and compensating for it.

12. Computer program element adapted to perform the method according to claim 1 when executed on a computer.

13. Apparatus for acquiring and dynamically visualizing coronary information comprising:
    an X-ray source (23 for emitting X-rays;
    an X-ray detector (25) configured to acquire first dynamic cardiac data during a first cardiac stage during which a contrast agent is detected in a first region and configured to acquire second dynamic cardiac data during a second cardiac stage during which said contrast agent is detected in a second region;
    a computing unit (31) configured to continuously superimpose the first and the second cardiac data, and
    a display unit (31) for displaying a representation of said superimposition which shows both the first and second regions with the contrast agent,
    wherein the first cardiac data and the second cardiac data corresponds to a same phase within a cardiac cycle and are visualized simultaneously, and wherein a cardiac stage defines a period of time where a certain amount or volume of blood with the contrast agent, passes certain stages of blood circulation.

14. Computer readable medium with a computer program element according to claim 12.

* * * * *